US009128077B2

United States Patent
Kaneko et al.

(10) Patent No.: US 9,128,077 B2
(45) Date of Patent: Sep. 8, 2015

(54) DETERIORATION ANALYSIS METHOD AND CHEMICAL STATE MEASUREMENT METHOD

(71) Applicant: SUMITOMO RUBBER INDUSTRIES, LTD., Kobe-shi, Hyogo (JP)

(72) Inventors: Fusae Kaneko, Kobe (JP); Hiroyuki Kishimoto, Kobe (JP)

(73) Assignee: SUMITOMO RUBBER INDUSTRIES, LTD., Kobe-shi (JP)

( * ) Notice: Subject to any disclaimer, the term of this patent is extended or adjusted under 35 U.S.C. 154(b) by 53 days.

(21) Appl. No.: 14/046,658

(22) Filed: Oct. 4, 2013

(65) Prior Publication Data

US 2014/0099723 A1 Apr. 10, 2014

(30) Foreign Application Priority Data

Oct. 5, 2012 (JP) ................................ 2012-223332
Dec. 6, 2012 (JP) ................................ 2012-267387

(51) Int. Cl.
*G01N 33/44* (2006.01)
*G01N 23/087* (2006.01)
*G01N 23/06* (2006.01)
*G01N 23/227* (2006.01)

(52) U.S. Cl.
CPC ............ *G01N 33/445* (2013.01); *G01N 23/063* (2013.01); *G01N 23/087* (2013.01); *G01N 23/2273* (2013.01); *Y10T 436/255* (2015.01)

(58) Field of Classification Search
CPC ..... G01N 23/00; G01N 23/06; G01N 23/063; G01N 23/083; G01N 23/087; G01N 23/2273; G01N 33/44; G01N 33/445; Y10T 436/25125; Y10T 436/255
USPC ................ 436/73, 80, 85, 164, 174, 175, 178
See application file for complete search history.

(56) References Cited

U.S. PATENT DOCUMENTS

| | | | | |
|---|---|---|---|---|
| 2013/0226470 | A1* | 8/2013 | Kaneko et al. | 702/34 |
| 2014/0349407 | A1* | 11/2014 | Kaneko et al. | 436/85 |

FOREIGN PATENT DOCUMENTS

| | | |
|---|---|---|
| JP | 05-099817 | 4/1993 |
| JP | 2003-213122 A | 7/2003 |
| JP | 2004-027032 | 1/2004 |

(Continued)

OTHER PUBLICATIONS

Ade et al., "NEXAFS Microscopy and Resonant Scattering: Composition and Orientation Probed in Real and Reciprocal Space", Polymer, 49, 2008, pp. 643-675.

(Continued)

*Primary Examiner* — Maureen Wallenhorst
(74) *Attorney, Agent, or Firm* — Birch, Stewart, Kolash & Birch, LLP

(57) ABSTRACT

The present invention provides a deterioration analysis method capable of analyzing in detail deterioration of a polymer material, and in particular deterioration in the surface condition of a polymer material with low conductivity. The present invention relates to a deterioration analysis method including irradiating a polymer material with a metal coating having a thickness of 100 Å or less formed thereon, with high intensity X-rays, and measuring X-ray absorption while varying the energy of the X-rays, to analyze deterioration of the polymer.

8 Claims, 5 Drawing Sheets

(56) References Cited

FOREIGN PATENT DOCUMENTS

| | | | |
|---|---|---|---|
| JP | 2011-141199 | A | 7/2011 |
| JP | 2012-141278 | A | 7/2012 |
| WO | WO 2012/081278 | A1 | 6/2012 |

OTHER PUBLICATIONS

Lippitz et al., Surface Analysis of Partially Crystalline and Amorphous Poly(Ethylene Terephthalate) Samples by X-ray Absorption Spectroscopy (NEXAFS), Polymer, vol. 37, No. 14, pp. 3151-3155, 1996.

Mochiji et al., "Soft X-ray Spectroscopy of Polymer Resist Using Synchrotron Radiation", Review of Scientific Instruments, 60, 1989, pp. 2160-2163.

Rastomjee et al., "Aluminium Metallisation of Argon and Oxygen Plasma-Modified Polycarbonate Thin Film Surfaces", Applied Surface Science, 136, 1998, pp. 280-297.

Winter et al., "The Thermal Ageing of Poly(3,4-ethylenedioxythiophene). An Investigation by X-ray absorption and X-ray Photoelectron Spectroscopy", Chemical Physics, 194, 1995, pp. 207-213.

Romero-Sanchez et al., Abstract of "Journal of Adhesion Science and Technology", Database Compendex, Engineering Information, Inc., 2005, XP002726189.

Abstract of "Journal of Adhesion Science and Technology", Database Compendex, Engineering Information, Inc., 1994, XP002726190.

Grythe et al., "Surface Modification of EPDM Rubber by Plasma Treatment", Langmuir, 2006, vol. 22, No. 14, pp. 6109-6124.

* cited by examiner

Before normalization

DETERIORATION ANALYSIS METHOD AND CHEMICAL STATE MEASUREMENT METHOD

TECHNICAL FIELD

The present invention relates to a deterioration analysis method for analyzing deterioration of polymer materials. The present invention also relates to a chemical state measurement method capable of accurately examining a change in chemical state on the surface of a rubber material, and in particular a change in chemical state occurring starting from the surface, such as deterioration.

BACKGROUND ART

In order to evaluate a change in chemical state of a polymer material containing at least one diene rubber due to deterioration, in general, methods such as an infrared spectroscopy (FT-IR), nuclear magnetic resonance analysis (NMR), and X-ray photoelectron spectroscopy (XPS) are used. FT-IR or NMR provides a detailed examination of the chemical state, but gives bulk information and therefore is difficult to use to examine in detail the chemical state after deterioration which proceeds from the sample surface.

Under such circumstances, there has been a demand to provide a method for examining the deterioration proceeding from the surface; for example, Patent Literature 1 proposes a method including irradiating a polymer material with high intensity X-rays, and measuring X-ray absorption while varying the energy of the X-rays, to analyze deterioration of the polymer, wherein the method includes a NEXAFS (Near Edge X-ray Absorption Fine Structure) method which measures an X-ray absorption spectrum near the absorption edge of a specific target element by using high intensity X-rays.

In the NEXAFS measurement, a method called the electron yield method which detects a current flowing when a sample is irradiated with X-rays is frequently used, which means that the sample generally needs to be an electrically conductive material. In general, polymer materials are insulating materials; however, when the sample is a tire rubber composition, particularly for sidewalls, for example, conductive carbon black is contained in a large amount, which ensures that even a relatively thick sample, such as having a thickness of about 1 mm, has conductivity and thus can be measured.

However, since tires have been required to have better fuel economy in recent years, there is a trend to decrease the amount of carbon black even in a sidewall rubber composition. Additionally, in the case of a tread rubber composition, there is a trend to add silica as a reinforcing agent to further decrease the amount of carbon black. In this way, recent fuel-efficient rubber formulations are less likely to ensure conductivity of the sample, and therefore such a sample having a thickness of about 1 mm is difficult to measure by NEXAFS.

The foregoing Patent Literature 1 also proposes processing (cutting) a polymer material with a microtome to be 100 μm or less, preferably 500 nm or less, in order to achieve a measurement with high S/B and S/N ratios. However, since the deterioration of a tire proceeds from the surface, it is necessary to cut the outermost surface and measure the outer surface side, but it is difficult to cut the outermost surface with a microtome. Even if the outermost surface can be cut, it is also difficult to determine which side of the prepared sample is the outer surface side.

As described above, on the basis of the conventional methods, it is difficult to examine in detail the deterioration proceeding from the sample surface by performing NEXAFS measurement of a sample poor in conductivity, such as particularly a tire rubber composition with a low carbon black content.

Meanwhile, as the method for examining a change in chemical state of a rubber material including a rubber component such as a diene rubber, and in particular a change in chemical state occurring starting from the surface of the rubber material, such as deterioration, for example, the following X-ray-based techniques are known: X-ray photoelectron spectroscopy (XPS method) and the method which measures an X-ray absorption spectrum near the absorption edge of a specific target element by using high intensity X-rays (NEXAFS method), as described above.

The XPS method and the NEXAFS method are each a surface-sensitive measurement technique with a detection depth ranging from the surface to a few tens of nanometers. In these methods, to examine the chemical state of polymers, for example, measurements targeting carbon are in general performed (e.g., a spectrum near the 1s orbital of carbon in the XPS method, and a spectrum near the carbon K-shell absorption edge in the NEXAFS method).

However, it is difficult for the conventional evaluation methods to accurately measure a change in chemical state on the surface of a sample such as a deteriorated rubber material. Therefore, there is a demand to provide an evaluation method capable of accurately measuring a change of the surface condition.

CITATION LIST

Patent Literature

Patent Literature 1: JP2012-141278A

SUMMARY OF INVENTION

Technical Problem

An object of the present invention is to solve the problems mentioned above and to provide a deterioration analysis method capable of analyzing in detail deterioration of a polymer material, and in particular deterioration in the surface condition of a polymer material with low conductivity.

Another object of the present invention is to solve the problems mentioned above and to provide a chemical state measurement method capable of accurately measuring a change in chemical state on the surface of a rubber material, and in particular a change in chemical state occurring starting from the surface, such as deterioration (namely, deterioration of the rubber material).

Solution to Problem

A first aspect of the present invention relates to a deterioration analysis method, including irradiating a polymer material with a metal coating having a thickness of 100 Å or less formed thereon, with high intensity X-rays, and measuring X-ray absorption while varying the energy of the X-rays, to analyze deterioration of the polymer.

In the deterioration analysis method, the metal coating is preferably a vapor deposited metal film.

In the deterioration analysis method, the polymer material is preferably a tire rubber composition. Here, the tire rubber composition preferably has a carbon black content of 50 parts by mass or less per 100 parts by mass of a rubber component of the tire rubber composition.

A second aspect of the present invention relates to a chemical state measurement method, including removing blooms on the surface of a rubber material and then applying an X-ray-based surface analysis method to measure the chemical state on the surface of the rubber material.

The chemical state measurement method preferably includes examining a change in chemical state occurring starting from the surface of the rubber material to measure deterioration of the rubber material.

The chemical state measurement method is preferably a method in which the blooms on the surface of the rubber material are removed using a solvent, suitably an organic solvent.

The chemical state measurement method is preferably a method in which the blooms on the surface of the rubber material are removed using a solvent extraction method.

Advantageous Effects of Invention

According to the first aspect of the present invention, the deterioration analysis method includes irradiating a polymer material with a metal coating having a thickness of 100 Å or less formed thereon, with high intensity X-rays, and measuring X-ray absorption while varying the energy of the X-rays, to analyze deterioration of the polymer; therefore, the deterioration analysis method can analyze in detail deterioration of the polymer material, and in particular deterioration in the surface condition of the polymer material with low conductivity. Accordingly, with respect to the deterioration of, for example, a tire rubber composition such as particularly a rubber composition with a low carbon black content and a silica-blended rubber composition, the deterioration analysis method can measure the deterioration degree (%), the contribution rates of the oxygen deterioration and ozone deterioration, and the amount of oxygen and ozone bonded to the polymer material (deterioration indicator).

According to the second aspect of the present invention, the chemical state measurement method includes removing blooms on the surface of a rubber material and then applying an X-ray-based surface analysis method to measure the chemical state on the surface of the rubber material; therefore, the chemical state measurement method can measure the exact chemical state on the surface of the rubber material. Accordingly, the chemical state measurement method can accurately measure a change in chemical state occurring starting from the surface, such as particularly deterioration, to evaluate deterioration of the rubber material.

BRIEF DESCRIPTION OF DRAWINGS

FIG. 1-2 is a graph showing the sample currents of a sample prepared by vapor depositing Au on a tire tread composition sample to a thickness of 8 Å and a tire tread composition sample without metal vapor deposition.

FIG. 1-3 is a (unnormalized) graph showing X-ray absorption spectra of polybutadiene rubber samples different in the thickness of the vapor deposited Au coating.

FIG. 1-4 is a graph (before normalization) showing the results of NEXAFS measurement of the carbon K-shell absorption edge of samples with a vapor deposited Au film formed thereon, which were prepared by vapor depositing Au on a fresh sidewall rubber composition sample, a sidewall rubber composition sample subjected to ozone deterioration for 48 hours, and a sidewall rubber composition sample subjected to oxygen deterioration for 1 week, respectively.

FIG. 1-5 is a graph (after normalization) showing the results of NEXAFS measurement of the carbon K-shell absorption edge of samples with a vapor deposited Au film formed thereon, which were prepared by vapor depositing Au on a fresh sidewall rubber composition sample, a sidewall rubber composition sample subjected to ozone deterioration for 48 hours, and a sidewall rubber composition sample subjected to oxygen deterioration for 1 week, respectively.

FIG. 1-6 is a graph showing the results of NEXAFS measurement near the oxygen K-shell absorption edge of samples with a vapor deposited Au film formed thereon, which were prepared by vapor depositing Au on a fresh sidewall rubber composition sample, a sidewall rubber composition sample subjected to ozone deterioration for 48 hours, and a sidewall rubber composition sample subjected to oxygen deterioration for 1 week.

FIG. 1-7 is a graph showing the results of NEXAFS measurement near the oxygen K-shell absorption edge of a sample with a vapor deposited Au film formed thereon, which was prepared by vapor depositing Au on a sidewall rubber composition sample subjected to complex deterioration (both oxygen deterioration and ozone deterioration).

FIG. 1-8 is a graph (after normalization) showing the results of NEXAFS measurement of samples with a vapor deposited Au film formed thereon, which were prepared by vapor depositing Au on sidewall rubber composition samples subjected to ozone deterioration for 24 hours and 48 hours, respectively.

FIG. 2-1 shows XPS spectra in the C1s region of a rubber material (with and without wiping).

FIG. 2-2 shows NEXAFS spectra near the carbon K-shell absorption edge (Example 2-1 and Comparative Examples).

DESCRIPTION OF EMBODIMENTS

Figure 1:
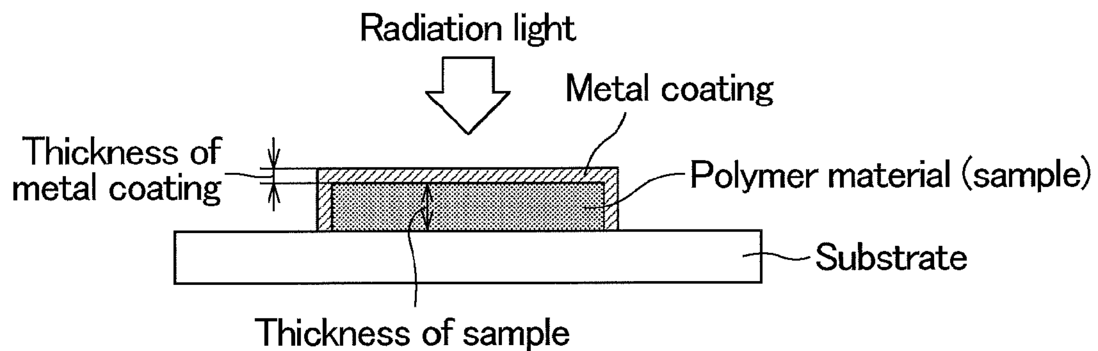
FIG. 1-1 is a schematic diagram illustrating a sample with a metal coating formed thereon.

The deterioration analysis method of the first aspect of the present invention includes irradiating a polymer material with a metal coating having a thickness of 100 Å or less formed thereon, with high intensity X-rays, and measuring X-ray absorption while varying the energy of the X-rays, to analyze deterioration of the polymer. It is known that the deterioration of a polymer material such as rubber is attributable to, for example, deterioration of polymer molecular chains and crosslinked structures due to ultraviolet light, oxygen, ozone, heat and the like. To improve the resistance to deterioration, it is important to know what factor is responsible and how the polymer molecular chains and crosslinked structures thereby change.

In this regard, the deterioration analysis method is a method capable of analyzing deterioration of a deteriorated polymer material by comparing spectra obtained by measuring X-ray absorptions while irradiating fresh and deteriorated polymer materials (samples) in which a metal coating of a predetermined thickness is preliminarily formed by, for example, a metal vapor deposition method to increase conductivity, with high intensity X-rays, the energy of the X-rays being varied during the measurement.

Specifically, a technique of measuring an X-ray absorption spectrum near the absorption edge of a specific target element by using high intensity X-rays (NEXAFS: Near Edge X-ray Absorption Fine Structure) may be applied to the polymer material with a metal coating of a predetermined thickness. Since the soft X-ray region includes absorption edges of light elements, the technique can analyze the chemical state of soft materials in detail.

In other words, in the first aspect of the present invention, the formation of a metal coating on the surface of a sample to prevent charging of the surface enables the NEXAFS measurement to be applied even to polymer materials poor in conductivity such as a rubber composition with a low carbon black content and a silica-blended rubber composition. In addition, the setting of the thickness of the metal coating at 100 Å or less to minimize the effect of the metal coating enables the deterioration analysis of the polymer material itself.

In the polymer material (sample) to be used in the first aspect of the present invention, a metal coating of a predetermined thickness is formed on the surface of the sample. This increases the conductivity of the polymer material (sample) to an extent enabling the deterioration analysis. The method for forming the metal coating is not particularly limited as long as the method is capable of forming the metal coating on the surface of a sample; for example, a metal vapor deposition method can suitably be used.

Examples of the method for performing metal vapor deposition include a resistance heating technique, an electron beam technique, a high frequency induction technique, a laser technique, and other techniques. In any of these techniques, a vapor deposition material is heated or vaporized in a vessel evacuated to vacuum, to form a thin film on the surface of a sample placed at a position away from the vapor deposition source. In consideration of the possibility that the vapor deposition material may be ionized to damage the sample, it is desirable to employ a resistance heating vacuum vapor deposition method which includes heating the vapor deposition material by applying an electrical current thereto, although any of those techniques can be used.

The thickness of the metal coating formed on the surface of the polymer material is 100 Å or less, preferably 50 Å or less, and more preferably 10 Å or less. When the thickness exceeds 100 Å, the vapor deposited metal tends to greatly affect the polymer material. In particular, the NEXAFS method is a surface-sensitive measurement; therefore, if the thickness of the deposited metal is large, then no exact chemical information about the sample itself may be obtained. The lower limit is not particularly limited as long as the conductivity is ensured, and the thickness of the metal coating is preferably 1 Å or more, more preferably 3 Å or more, and further preferably 5 Å or more.

In the NEXAFS method, X-ray energy is used for scanning, and thus a continuous X-ray generator is needed as the light source. For a detailed analysis of the chemical state, it is necessary to measure an X-ray absorption spectrum with a high S/N ratio and a high S/B ratio. For these reasons, a synchrotron is best used in the NEXAFS measurement because it emits X-rays having a brilliance of at least $10^{10}$ (photons/s/mrad$^2$/mm$^2$/0.1% bw) and is a continuous X-ray source. It is to be noted that the symbol bw indicates a band width of X-rays emitted from a synchrotron.

The brilliance (photons/s/mrad$^2$/mm$^2$/0.1% bw) of the high intensity X-rays is preferably $10^{10}$ or more, and more preferably $10^{12}$ or more. The number of photons (photons/s) of the high intensity X-rays is preferably $10^7$ or more, and more preferably $10^9$ or more. These upper limits are not particularly limited, and it is preferable to use an X-ray intensity low enough not to cause radiation damage.

The energy range over which scanning is made with high intensity X-rays is preferably 4000 eV or less, more preferably 1500 eV or less, and further preferably 1000 eV or less. If the energy range exceeds 4000 eV, the deterioration of a target polymer composite material may not be analyzed. The lower limit of the energy range is not particularly limited.

The measurement can be performed on the basis of a method in which a sample placed in ultra-high vacuum is irradiated with soft X-rays so that photoelectrons are emitted, then electrons flow from the ground into the sample so as to compensate for the emitted photoelectrons, and the sample current thus generated is measured.

More specifically, the measurement can be performed by the below-described method.

A sample with a metal coating of a predetermined thickness formed thereon is mounted on a sample holder and is then placed in a vacuum chamber for X-ray absorptiometry. FIG. 1-1 shows a schematic diagram illustrating the sample with a metal coating formed thereon. Subsequently, continuous X-rays emitted from a synchrotron are monochromatized with a monochromator, and then the sample is irradiated with the monochromatized X-rays. At that time, secondary electrons and photoelectrons escape from the sample surface into vacuum, and then electrons are replenished from the ground to compensate for the lost electrons. Then, the X-ray absorption (μL) is determined using the following formula, wherein the X-ray absorption intensity I represents a current flowing from the ground, and the incident X-ray intensity $I_0$ represents a current from a gold mesh provided in an optical system of a beamline (electron yield method). It should be noted that the Lambert-Beer formula is applicable to this technique, and the following formula is thought to hold approximately in the case of the electron yield method.

(Formula)

$$I_0(E)/I(E)=\exp(\mu L)\approx\mu L$$

(E: X-ray energy, L: Thickness of sample, μ: Absorption coefficient)

As the NEXAFS measurement method, the following three methods are typically used. In examples of the first aspect of the present invention, the electron yield method is used to perform the measurement but is not intended to limit the scope of the invention. Various detection methods may be used, and may be combined for simultaneous measurement.

(Transmission Method)

The transmission method is a method of detecting the intensity of the X-rays having passed through a sample. For the measurement of the intensity of transmitted light, for example, a photodiode array detector may be used.

(Fluorescence Method)

The fluorescence method is a method of detecting the fluorescent X-rays generated when a sample is irradiated with X-rays. The fluorescence method is effective for measuring an X-ray absorption spectrum of an element contained in a small amount. In addition, since fluorescent X-rays have high penetrating power, the fluorescent X-rays generated inside a sample can be detected. Hence, the fluorescence method is a most suitable method for obtaining bulk information.

(Electron Yield Method)

The electron yield method is a method of detecting a current flowing when a sample is irradiated with X-rays. Thus, the sample needs to be an electrically conductive material. In the first aspect of the present invention, the conductivity can be ensured by forming a metal coating. Moreover, when a polymer material is processed (cut) with a microtome to 100 μm or less, preferably 10 μm or less, more preferably 1 μm or less, and further preferably 500 nm or less, a measurement with high S/B and S/N ratios can be accomplished. For the purpose of ensuring the conduction between the substrate and the sample, a tape that has good conductivity and can be used even in vacuum, such as a carbon tape and a silver tape, may also be used.

Moreover, the features of the electron yield method include surface sensitivity (sensitivity to information about the sample surface up to a depth of approximately several nanometers). When a sample is irradiated with X-rays, electrons escape from elements. Here, since electrons strongly interact with substances, their mean free path in a substance is short. Further, since the energy of X-rays used in the NEXAFS method is relatively low, the kinetic energy of the escaped electrons is small. These facts mean that the electrons capable of jumping out of the sample surface are the electrons located in the very superficial layer of the sample. This is why the present detection method is a surface sensitive technique.

Now, the fact that the formation of a metal coating on the surface of a sample enables the measurement of X-ray absorption, and the fact that the thickness of the metal coating affects the analysis of deterioration of the sample will be specifically described with reference to FIGS. 1-2 and 1-3.

Figures 1, 2:
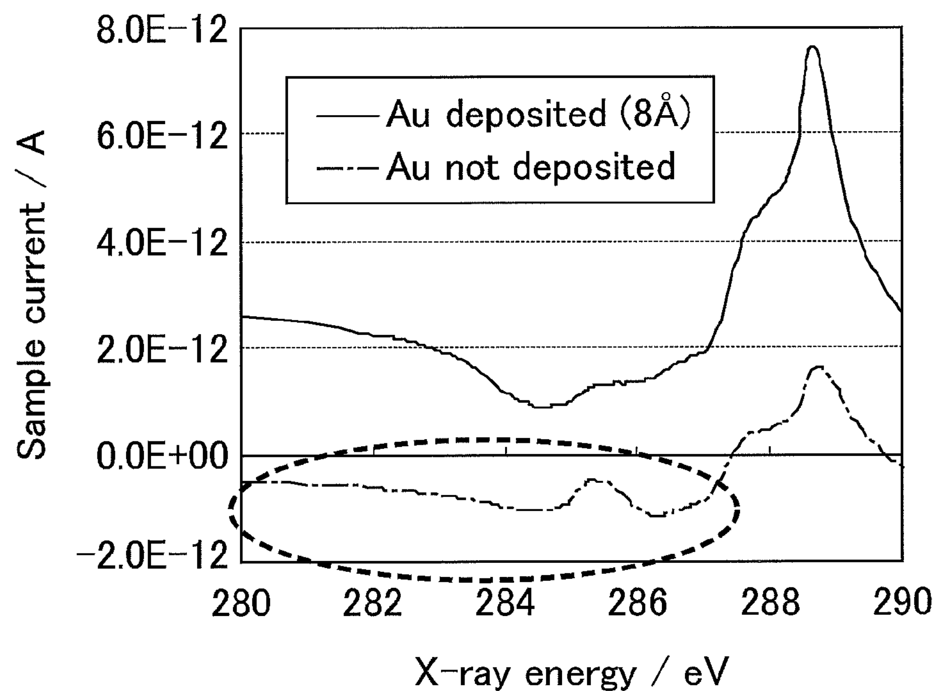

FIG. 1-2 shows the sample currents of a sample prepared by vapor depositing Au on a tire tread composition sample to a thickness of 8 Å and a tire tread composition sample without metal vapor deposition. The sample without metal vapor deposition showed negative values in the region surrounded by the dashed line which indicate that the measurement of X-ray absorption was unable to be performed. In contrast, the sample with Au vapor-deposited thereon showed the positive sample current which indicates that the measurement of X-ray absorption was able to be performed. Thus, the formation of a metal coating of a predetermined thickness on a sample enables the measurement of X-ray absorption of even a polymer material poor in conductivity.

The metal to be vapor deposited is preferably a metal having no X-ray absorption in the measurement energy range. For example, when the measurement near the carbon K absorption edge (270 eV to 320 eV) is performed, gold (Au), which has no absorption in this energy region, can be suitably used.

Figures 1, 2, 3:
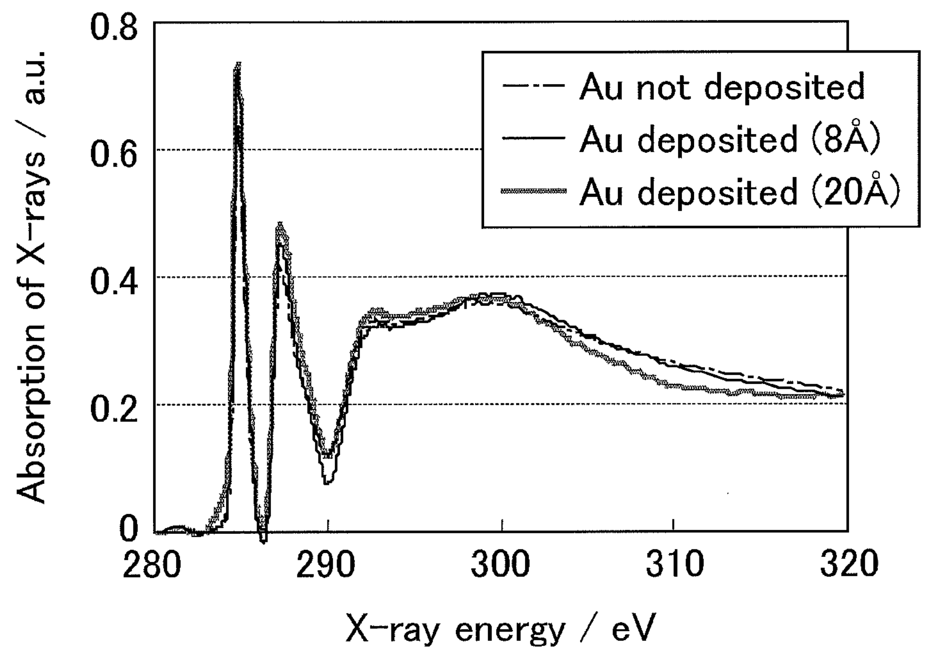
Figures 1, 2, 3, 4:
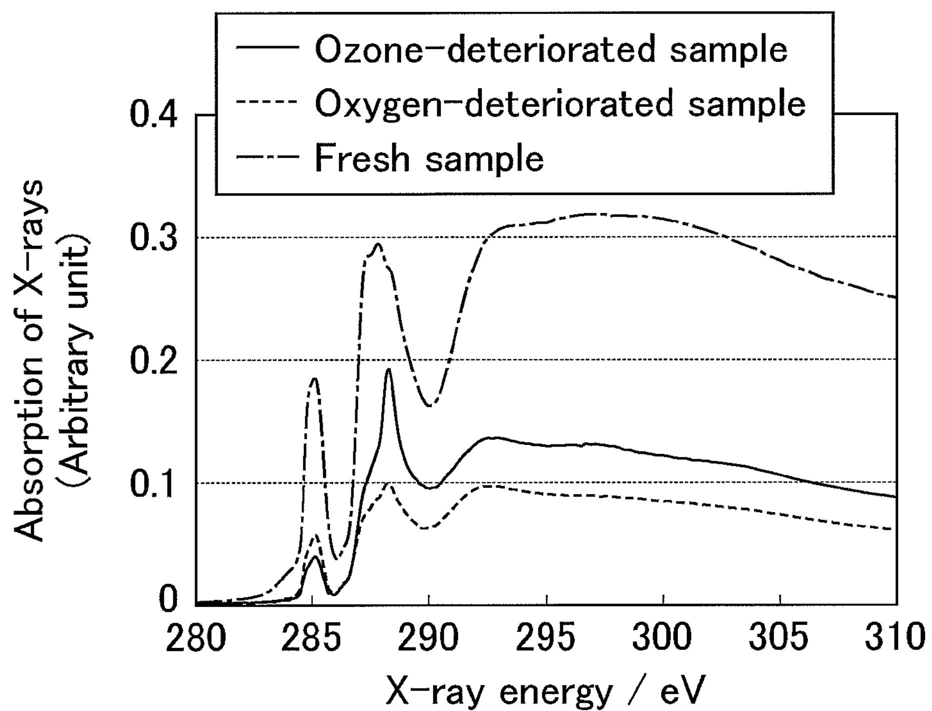
Figures 1, 2, 3, 4, 5:
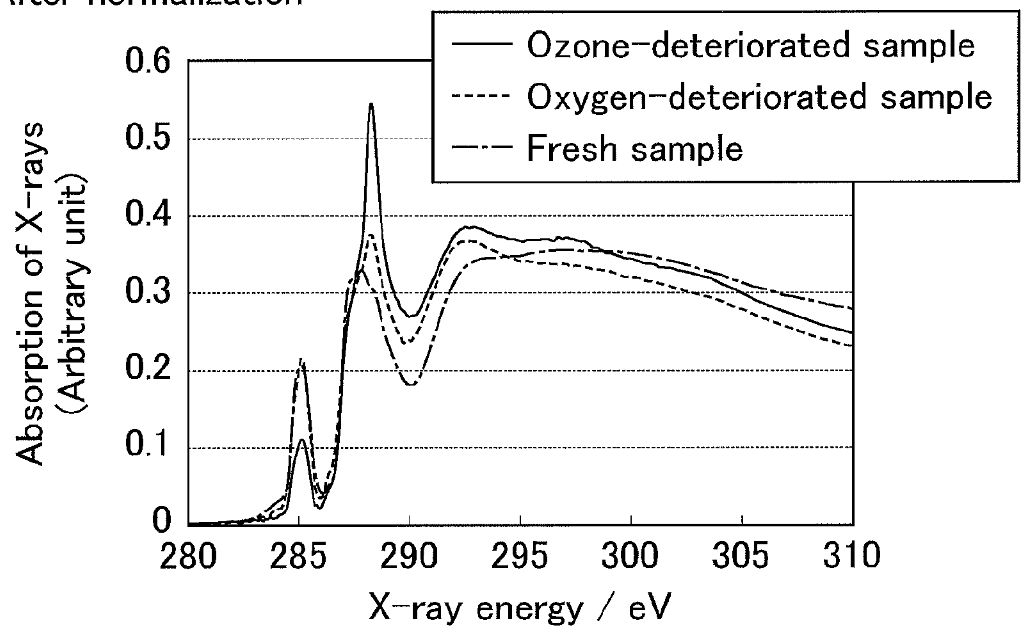
Figures 1, 2, 3, 4, 5, 6:
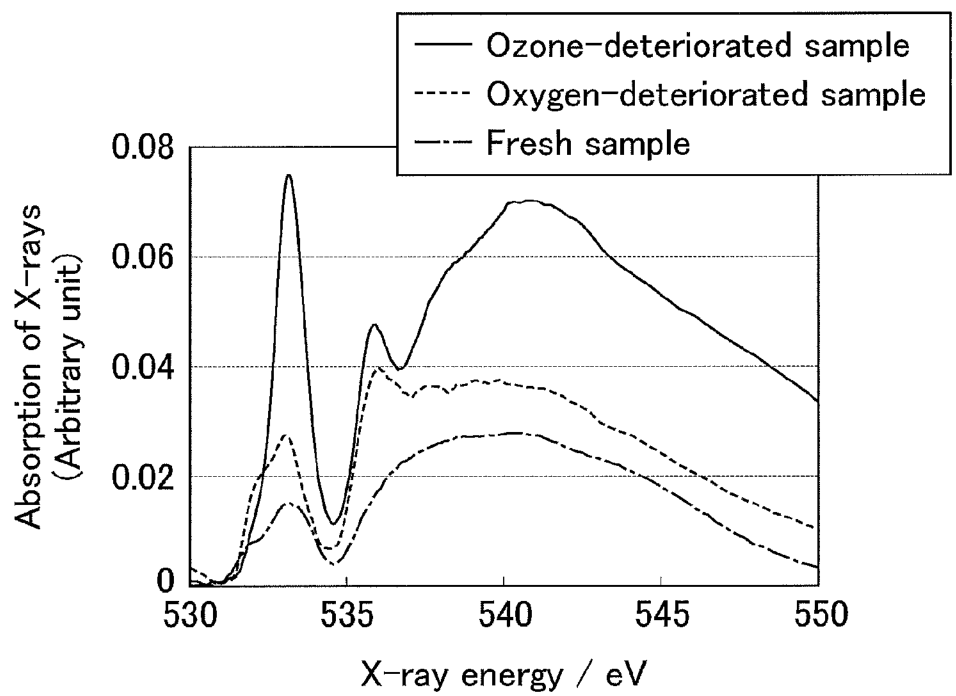
Figures 1, 2, 3, 4, 5, 6, 7:
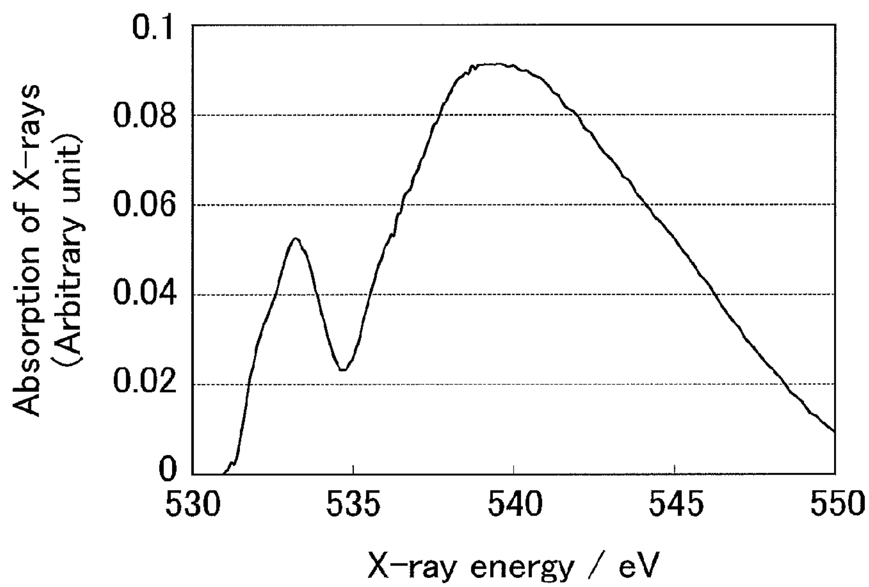
Figures 1, 2, 3, 4, 5, 6, 7, 8:
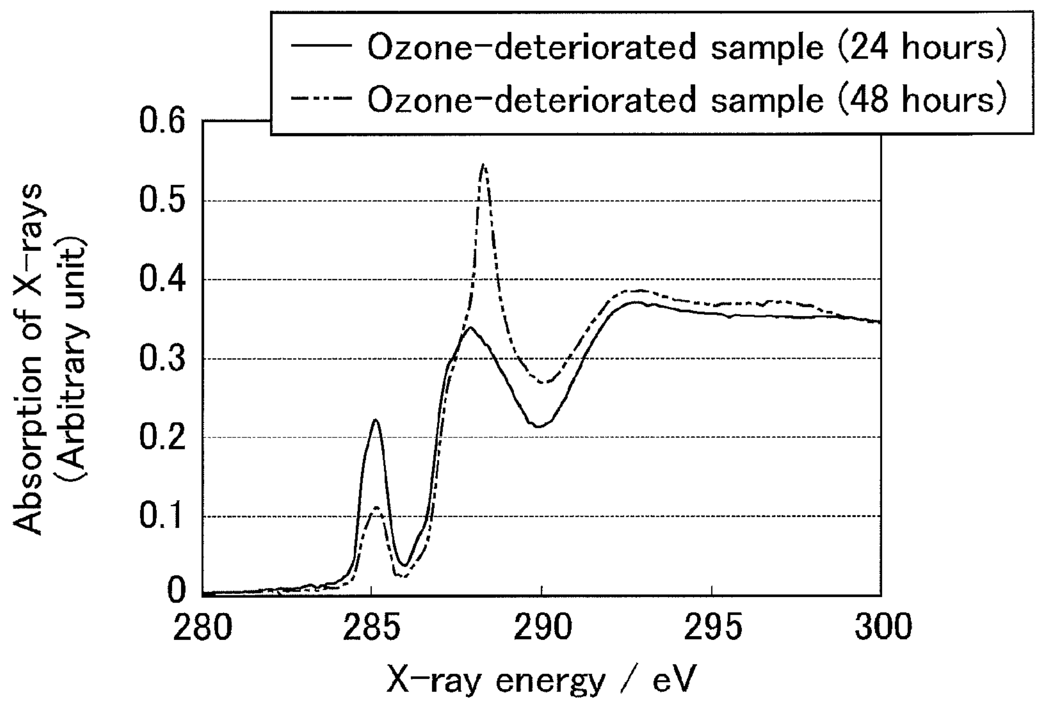
Figures 1, 2:
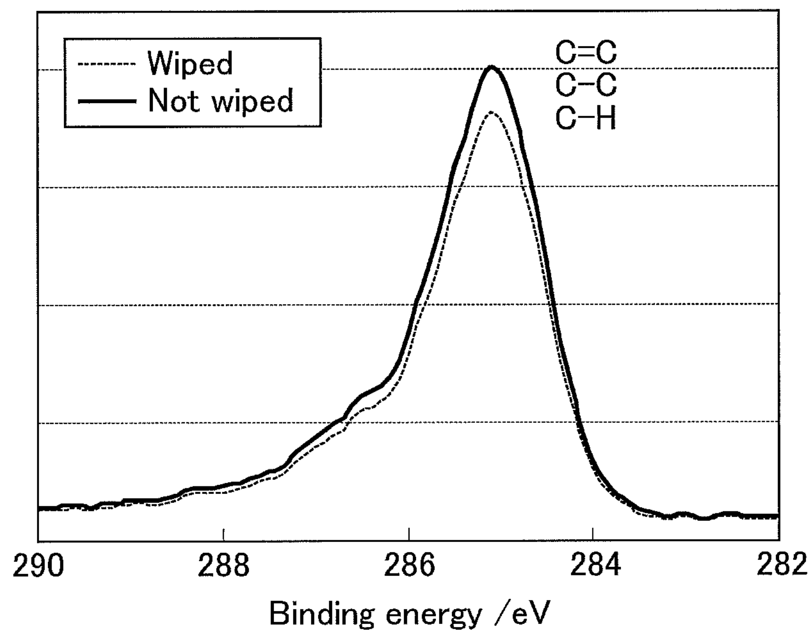
Figure 2:
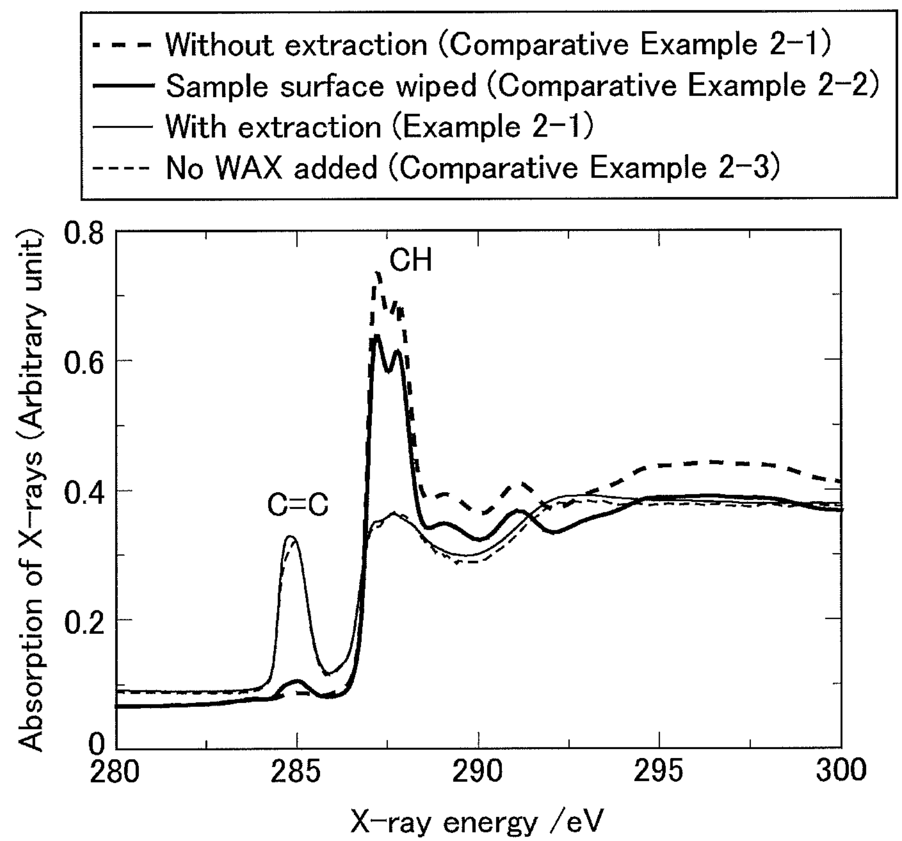

FIG. 1-3 shows X-ray absorption spectra of polybutadiene rubber samples each with a vapor deposited Au film having a different thickness formed thereon. Here, a cast film is used and thus even the sample without metal vapor deposition can be measured. Accordingly, this experiment is to investigate the variation of the X-ray absorption spectra when the vapor deposition thickness is varied. The larger the variation, the more greatly the vapor deposited metal affects the X-ray absorption, which indicates that an accurate deterioration analysis tends to be unfeasible.

The X-ray absorption spectra in FIG. 1-3 show that starting from the spectrum of the sample without any vapor deposited Au film formed thereon, the shape of the spectrum gradually changes, that is to say, the spectrum becomes affected by the vapor deposited film, with the increase of the thickness of the vapor deposited film. More specifically, FIG. 1-3 shows that the spectrum of the sample with an 8 Å-thick vapor deposited Au film formed thereon is almost exactly the same as that of the sample without any vapor deposited film formed thereon, whereas the spectrum of the sample with a 20 Å-thick vapor deposited Au film formed thereon is slightly different in shape, which indicates that the spectrum may be somewhat affected by the vapor deposited film. It should be noted that the deterioration analysis is feasible even with the thickness of 20 Å although the accuracy of the analysis is somewhat lower.

When the electron yield method is used to measure and analyze an X-ray absorption spectrum of a polymer material with a metal coating having a thickness of 100 Å or less formed thereon (hereinafter, also referred to as the metal-coated sample), the deterioration degree (%), the contribution rates (%) of oxygen deterioration and ozone deterioration, and the amount of oxygen and ozone bonded (deterioration indicator) can be analyzed. Hereinafter, each of these items is described.

The deterioration analysis method may be a method including calculating normalization constants $\alpha$ and $\beta$ using the following formula 1-1 on the basis of X-ray absorption spectra obtained by scanning over a required range of high intensity X-ray energies at the carbon K-shell absorption edge within the range of 260 eV to 400 eV; performing waveform separation of the X-ray absorption spectra at the carbon K-shell absorption edge corrected with the normalization constants $\alpha$ and $\beta$ to obtain peak areas derived from $\pi^*$ transition at around 285 eV; and determining the deterioration degree using the following formula 1-2 with the obtained peak areas:

[total area of X-ray absorption spectrum over measurement range of metal-coated sample before deterioration]×$\alpha$=1, and

[total area of X-ray absorption spectrum over measurement range of metal-coated sample after deterioration]×$\beta$=1; and (formula 1-1)

[1-[(peak area of $\pi^*$ after deterioration)×$\beta$]/[(peak area of $\pi^*$ before deterioration)×$\alpha$]]×100=deterioration degree (%). (formula 1-2)

In this manner, the deterioration degree (%) of a deteriorated polymer can be obtained to analyze the deterioration rate. In the method for determining the deterioration degree, the range of high intensity X-ray energies is preferably set to 260 to 350 eV. In the method for determining the deterioration degree, the background is assessed based on a slope before the absorption edge and subtracted prior to the operation of the foregoing formula 1-1.

In the method for determining the deterioration degree, the total area of the X-ray absorption spectrum in the formula 1-1 is the integral of the spectrum over the measurement range, and the energy range can be altered according to the measurement conditions and the like.

The method for determining the deterioration degree is more specifically described using an example in which a fresh sidewall rubber composition sample, a sidewall rubber composition sample subjected to ozone deterioration for 48 hours, and a sidewall rubber composition sample subjected to oxygen deterioration for 1 week are used.

FIG. 1-4 shows the results of NEXAFS measurement of the carbon K-shell absorption edge of samples with a vapor deposited Au film formed thereon, which were prepared by vapor depositing Au on a fresh sample, an ozone deteriorated sample, and an oxygen deteriorated sample, respectively. As shown in FIG. 1-4, each of the deteriorated samples has a smaller $\pi^*$ peak at around 285 eV than that of the fresh sample; however, it is difficult for the NEXAFS method to perform an absolute measurement. This is because subtle changes in the distance from the light source to the sample or other parameters affect the magnitude of the X-ray absorption spectrum. For this reason, the results of NEXAFS measurement of the carbon K-shell absorption edge cannot be simply compared between samples.

For comparison between the measured X-ray absorption spectra of the samples, normalization is then carried out as follows (the X-ray absorption spectrum of each sample is corrected for direct comparison). Since the amount of carbon shell X-ray absorption is not changed before and after deterioration, the peak area of the carbon K-shell absorption edge is normalized to 1 using the formula 1-1. In other words, first, normalization constants $\alpha$ and $\beta$ are calculated using the formula 1-1 on the basis of the X-ray absorption spectra before normalization, and then the spectra are corrected (normalized) by multiplying the X-ray absorption spectra before normalization by $\alpha$ and $\beta$, respectively, whereby the $\pi^*$ peaks of the samples can be directly compared.

FIG. 1-5 shows the thus-obtained spectra at the carbon K-shell absorption edge after normalization. The deterioration degree is determined using the formula 1-2 based on the normalized spectra. The deterioration degree is the rate of reduction of the $\pi^*$ peak from before to after deterioration, and indicates the deterioration rate (%) of a sample.

In the method for determining the deterioration degree, the deterioration degree can be similarly determined when the peak intensities are used instead of the peak areas in the formula 1-2.

The deterioration analysis method may also be a method including performing waveform separation of an X-ray absorption spectrum at the oxygen K-shell absorption edge obtained by scanning over a range of high intensity X-ray energies of 500 to 600 eV; and calculating contribution rates of oxygen deterioration and ozone deterioration using the following formula 1-3, wherein the oxygen deterioration corresponds to a peak on the low energy side with a peak top energy in the range of 532 to 532.7 eV, and the ozone deterioration corresponds to a peak on the high energy side with a peak top energy in the range of 532.7 to 534 eV:

[peak area of oxygen deterioration]/[(peak area of ozone deterioration)+(peak area of oxygen deterioration)]×100=contribution rate (%) of oxygen deterioration, and

[peak area of ozone deterioration]/[(peak area of ozone deterioration)+(peak area of oxygen deterioration)]×100=contribution rate (%) of ozone deterioration. (formula 1-3)

In this manner, contribution rates (%) of oxygen deterioration and ozone deterioration in a deteriorated polymer material can be obtained to analyze the contribution rate of each deterioration factor. In the method for calculating the contribution rates, the background is assessed based on a slope before the absorption edge and subtracted prior to the operation of the forgoing formula 1-3.

The method for calculating the contribution rates is more specifically described using an example in which a fresh sidewall rubber composition sample, a sidewall rubber composition sample subjected to ozone deterioration for 48 hours, and a sidewall rubber composition sample subjected to oxygen deterioration for 1 week are used.

First, FIG. 1-6 shows the results of NEXAFS measurement near the oxygen K-shell absorption edge of samples with a vapor deposited Au film formed thereon, which were prepared by vapor depositing Au on a fresh sample, an ozone deteriorated sample and an oxygen deteriorated sample, respectively. The ozone deteriorated sample has a peak at 532.7 to 534 eV, whereas the oxygen deteriorated sample has a peak at 532 to 532.7 eV, and one of the two peaks, which is on the high energy side, is derived from ozone deterioration and the other peak on the low energy side is derived from oxygen deterioration.

Moreover, FIG. 1-7 shows the results of NEXAFS measurement of a sample with a vapor deposited Au film formed thereon, which was prepared by vapor depositing Au on a sample subjected to complex deterioration (both oxygen deterioration and ozone deterioration). As shown in FIG. 1-7, a peak with two shoulders was detected at 532 to 534 eV. This is thought to be due to superposition of the low-energy side peak (532 to 532.7 eV) from oxygen deterioration and the high-energy side peak (532.7 to 534 eV) from ozone deterioration. Hence, peak separation was performed and then the contribution rates of oxygen deterioration and ozone deterioration were determined using the formula 1-3. In this manner, a sample in which both oxygen deterioration and ozone deterioration have proceeded can be analyzed for the proportion of each of the two deterioration factors, oxygen deterioration and ozone deterioration.

In the method for calculating the contribution rates, the contribution rates of oxygen deterioration and ozone deterioration can be similarly determined when the peak intensities are used instead of the peak areas in the formula 1-3.

The deterioration analysis method may also be a method including determining a normalization constant $\gamma$ using the following formula 1-4 on the basis of an X-ray absorption spectrum at the carbon K-shell absorption edge after deterioration; and correcting a total peak area of the oxygen K-shell absorption edge with the normalization constant $\gamma$ based on the following formula 1-5 to determine the amount of oxygen and ozone bonded to the polymer material:

[total area of X-ray absorption spectrum at carbon K-shell absorption edge]×$\gamma$=1; and (formula 1-4)

[peak area of oxygen K-shell absorption edge]×$\gamma$=amount (index) of oxygen and ozone bonded. (formula 1-5)

In this manner, the amount of oxygen and ozone bonded to a polymer material due to deterioration can be measured and used as a deterioration indicator.

In the method for determining the bonded amount, the total peak area is the integral of the spectrum over the measurement range, and the energy range can be altered according to the measurement conditions and the like.

The method for determining the bonded amount is more specifically described using an example in which sidewall rubber composition samples subjected to ozone deterioration for 24 hours and 48 hours, respectively, are used.

FIG. 1-8 shows the results of NEXAFS measurement of samples with a vapor deposited Au film formed thereon, which were prepared by vapor depositing Au on the above samples. These spectra are each obtained by calculating a normalization constant $\gamma$ using the formula 1-4 on the basis of an X-ray absorption spectrum at the carbon K-shell absorption edge, and carrying out normalization as mentioned above. The normalized peak area of the oxygen K-shell absorption edge is thought to correspond to the amount of oxygen and ozone bonded. As shown in the FIG. 1-8, the sample subjected to deterioration for 48 hours shows a larger area than the sample subjected to deterioration for 24 hours, which confirms that the thus-obtained value can be used as a deterioration index. A larger numerical value of the deterioration index indicates a larger amount of oxygen bonded to the polymer material due to deterioration. In this manner, the deterioration rate when oxygen or ozone is bonded to a polymer material can be measured based on the rate of increase in the peak area of the oxygen K-shell absorption edge.

The aforementioned method of the first aspect of the present invention can be carried out using, for example, the BL12 beamline at Kyushu Synchrotron Light Research Center (SAGA-LS).

The polymer material applicable to the first aspect of the present invention is not particularly limited, and may be any conventionally known material. For example, the polymer material may suitably be a rubber material containing at least one diene rubber, or a composite material combining the rubber material and at least one resin. Examples of the diene rubber include: double bond-containing polymers such as natural rubber (NR), isoprene rubber (IR), butadiene rubber (BR), styrene-butadiene rubber (SBR), acrylonitrile-butadiene rubber (NBR), chloroprene rubber (CR), butyl rubber (IIR), halogenated butyl rubber (X-IIR) and styrene-isoprene-butadiene rubber (SIBR).

Examples of the resin include, but not limited to: resins widely used in the field of rubber industry, such as C5 aliphatic petroleum resins, cyclopentadiene petroleum resins, and other petroleum resins.

The first aspect of the present invention can be applied to both materials with high conductivity and materials with low conductivity, without any limitations; for example, the first aspect of the present invention can be suitably applied to tire rubber compositions including a rubber component as the polymer material and filler such as silica and carbon black. Examples of the rubber component include diene rubbers mentioned above. The carbon black and silica are not particularly limited, and may be those widely used in the tire field.

Since the method of the first aspect of the present invention is applicable to polymer materials having any conductivity, the carbon black content in the tire rubber composition is not particularly limited. In particular, since the conductivity is ensured by the metal coating, the first aspect of the present invention is applicable even to rubber compositions having a carbon black content of 50 parts by mass or less per 100 parts by mass of the rubber component, and is also applicable even to those having a carbon black content of 20 parts by mass or less.

The first aspect of the present invention is also applicable to silica-blended rubber compositions with low conductivity. Here, the silica content in the tire rubber composition is not particularly limited, and is preferably 5 to 90 parts by mass, and more preferably 10 to 60 parts by mass, per 100 parts by mass of the rubber component.

The tire rubber composition may appropriately contain, in addition to the components mentioned above, compounding ingredients commonly used in the production of a rubber composition, such as a reinforcing filler such as clay, a silane coupling agent, zinc oxide, stearic acid, various antioxidants, oil, wax, a vulcanizing agent and a vulcanization accelerator.

The tire rubber composition can be prepared by an ordinary method. Specifically, the tire rubber composition can be prepared, for example, by a method in which the components are kneaded with a device such as a Banbury mixer, a kneader or an open roll mill, and subsequently the resulting mixture is vulcanized. The rubber composition can be used for various tire components and, in particular, can be suitably used for treads and sidewalls, for example.

The first aspect of the present invention is also applicable to pneumatic tires produced by a usual method using the tire rubber composition. The pneumatic tire can be produced as follows: the tire rubber composition including the components, before vulcanization, is extrusion processed into the shape of a tire component such as a sidewall or tread, and then molded together with other tire components in a tire building machine by an ordinary method to form an unvulcanized tire, and the unvulcanized tire is pressurized under heating in a vulcanizer to produce a tire.

The method of the first aspect of the present invention can be applied to samples (polymer materials) taken from, for example, tire rubber compositions or various tire components including the rubber compositions after a metal coating of a predetermined thickness is formed on the samples. Here, the thickness of the sample is not particularly limited, and is preferably 10 nm to 1 mm, and more preferably 50 nm to 100 μm.

The chemical state measurement method of the second aspect of the present invention includes removing blooms on the surface of a rubber material and then applying an X-ray-based surface analysis method to measure the chemical state on the surface of the rubber material.

As the method for examining the surface condition of a rubber material containing a diene rubber or the like, the following methods are used: measurement of, for example, a spectrum near the is orbital of carbon or a spectrum near the carbon K-shell absorption edge, namely, measurement of spectra associated with carbon, by a surface-sensitive technique such as the XPS method or the NEXAFS method. In general, such a rubber material contains chemicals such as wax and an antioxidant, and these chemicals crystallize out (or bloom) on the surface and thereby serve to suppress deterioration.

Here, the blooming wax is a hydrocarbon and is formed from carbon just like rubber. Therefore, it is inferred that in order to examine, using a surface-sensitive technique, the exact chemical state of rubber on the surface of a rubber material that has undergone a change in chemical state due to deterioration or the like, it is necessary to remove blooms (surface deposits including wax, antioxidants and the like) which possibly adversely affect the spectrum, or in other words, to remove carbon components other than rubber in advance.

Conventionally, when the surface of a rubber material that has undergone a change in chemical state due to deterioration or the like is examined by, for example, the XPS method, a pretreatment such as wiping the surface of the rubber material with waste made of paper (e.g. Kimwipe manufactured by Nippon Paper Crecia Co., Ltd.) wetted with acetone is performed prior to the measurement.

FIG. 2-1 shows XPS spectra in the C1s region of a sample subjected to such a wiping treatment of the surface of a rubber material and a sample not subjected to the treatment. The figure demonstrates spectral difference between with and without wiping. As shown in FIG. 2-1, the XPS method allows the peaks of C—C bond and C—H bond in wax and the peak of C═C bond in rubber to appear as one and the same peak. Thus, the spectral intensity varies according to whether or not the wiping treatment is performed, but the spectral shape remains unchanged; therefore, at present, measurement is performed without being able to accurately verify whether or not blooms such as wax have been sufficiently removed.

As described above, the conventional techniques cannot measure the exact chemical state on the surface; in contrast, the method of the second aspect of the present invention can measure the exact chemical state on the surface of a rubber material because the effects of carbon components other than rubber, such as wax, can be eliminated by removing blooms on the rubber surface using, for example, a solvent in advance before performing a surface analysis such as the XPS method or NEXAFS method. Accordingly, the exact chemical state can be measured based on an XPS spectrum or NEXAFS spectrum; moreover, a comparison between the spectra measured before and after deterioration also enables to accurately measure deterioration (deterioration degree).

In the second aspect of the present invention, first, blooms on the surface of a rubber material are removed.

The rubber material to be used in the second aspect of the present invention is not particularly limited and may be any conventionally known rubber composition. Examples thereof include rubber compositions including a rubber component, wax, an antioxidant and the like.

Examples of the rubber component include diene rubbers mentioned above. The rubber component may be one containing one or more modifying groups such as a hydroxyl group and an amino group.

Moreover, the rubber component may be a composite material combining the foregoing rubber component and at least one resin. Examples of the resin include resins mentioned above.

Examples of the wax include, but not limited to: petroleum wax and natural wax. Examples of the petroleum wax include paraffin wax and microcrystalline wax. Examples of the natural wax include: plant waxes such as candelilla wax and carnauba wax; animal waxes such as beeswax and lanolin; and mineral waxes such as ozocerite.

The antioxidant is not particularly limited and may be any antioxidant used in the rubber field. Examples thereof include: amine antioxidants (e.g. naphthylamine, diphenylamine and p-phenylenediamine antioxidants), quinoline antioxidants, hydroquinone derivatives, phenolic antioxidants (e.g. monophenol, bisphenol, trisphenol and polyphenol antioxidants), thiobisphenol antioxidants, imidazole antioxidants (e.g. benzoimidazole antioxidants), thiourea antioxidants, phosphorous acid antioxidants, organic thioacid antioxidants, and carbamic acid metal salts.

The rubber material may appropriately contain compounding ingredients conventionally known in the rubber field, such as filler such as carbon black and silica, a silane coupling agent, zinc oxide, stearic acid, oil, a vulcanizing agent, a vulcanization accelerator and a cross-linking agent. Such a rubber material (rubber composition) can be prepared by a known kneading method, for example. Examples of the rubber material include rubber materials for tires (tire rubber compositions).

The method for removing blooms is not particularly limited as long as the method can remove blooms made of wax, antioxidants and the like; for example, a method using a solvent may be mentioned. As the removal method, a method using a tool such as a spatula is also possible, but is thought to be less likely to completely remove blooms, just like the method of wiping the surface with waste, for example; moreover, the method using a tool possibly changes the chemical state of the rubber itself. Therefore, this method is unsuitable.

Examples of the method for removing blooms using a solvent include: a method in which blooms are moistened (impregnated) with a solvent under predetermined conditions such as at room temperature or under heating; and an extraction method (solvent extraction method) in which, for example, solvent extraction is performed using an extractor such as a Soxhlet extractor. Among these, from the viewpoint of the capability of efficiently removing blooms, an extraction method such as Soxhlet extraction is preferred, and Soxhlet extraction is particularly preferred.

As the Soxhlet extraction, for example, an extraction operation based on the Soxhlet extraction according to JIS K6229 can be carried out. For example, a solvent (medium) is filled in an extraction flask disposed in the lowermost part of a Soxhlet extractor, a predetermined amount of a rubber material prepared as appropriately sized test pieces is placed in a paper or sintered glass vessel disposed in the intermediate part, and a condenser tube is connected to the uppermost part, whereby the Soxhlet extraction can be performed.

The extraction time in the extraction such as Soxhlet extraction is not particularly limited as long as blooms can be removed and the chemical state of the rubber is not changed during the extraction time. The extraction time may be appropriately set according to the components of the rubber material applied to the second aspect of the present invention. For example, the extraction time in Soxhlet extraction is preferably 10 to 36 hours. If the extraction time is less than 10 hours, blooms on the surface may not be sufficiently removed, whereas if the extraction time exceeds 36 hours, even the rubber molecules shortened due to deterioration may also be removed.

In the removal (moistening, extraction) using a solvent, the usable solvent may suitably be an organic solvent. Examples of the organic solvent include: monohydric alcohols such as methanol, ethanol, propanol and butanol; polyhydric alcohols such as ethylene glycol, propylene glycol and butylene glycol; ketones such as acetone and methyl ethyl ketone; esters such as methyl acetate and ethyl acetate; acyclic and cyclic ethers such as tetrahydrofuran and diethyl ether; polyethers such as polyethylene glycol; halogenated hydrocarbons such as dichloromethane, chloroform and carbon tetrachloride; hydrocarbons such as hexane, cyclohexane and petroleum ether; and aromatic hydrocarbons such as benzene and toluene. Among these, highly polar organic solvents are preferred, and acetone or ethanol is more preferred, because they can sufficiently remove blooms such as wax on the surface. These solvents may be used alone or in combinations of two or more.

In the second aspect of the present invention, after blooms on the surface of a rubber material are removed in advance, an X-ray-based surface analysis method is applied to the obtained sample (rubber material subjected to the removal treatment). Such a surface analysis method is preferably, for example, an XPS method (X-ray photoelectron spectroscopy) or a NEXAFS (Near Edge X-ray Absorption Fine Structure) method from the viewpoint of the capability of accurately measuring the chemical state on the surface of a rubber material.

Here, the XPS method may be a conventionally known method; for example, measurement of a spectrum near the is orbital of carbon can be performed to examine the chemical state on the surface. The NEXAFS method can be performed, for example, by the technique described in JP2012-141278A (which is incorporated by reference in its entirety) to examine the chemical state on the surface; more specifically, the NEXAFS method can examine the chemical state by measuring a spectrum near the carbon K-shell absorption edge, for example.

In the second aspect of the present invention, the application of the XPS method to a rubber material (sample) from which blooms on the surface are sufficiently removed by, for example, solvent extraction, enables to sufficiently suppress the effects of wax and antioxidants to measure the exact chemical state. Accordingly, in the XPS spectra of a rubber material before and after deterioration, the peaks of C—C bond and C—H bond, which are derived from wax, do not appear while the peak of C═C bond in rubber appears; therefore, it is possible to examine the exact chemical state of rubber on the surface of a rubber material both before and after deterioration. Further, a comparison between the peak intensities or areas of C═C bond before and after deterioration also enables to examine deterioration (deterioration degree).

Similarly, the application of the NEXAFS method to the sample enables to measure the exact chemical state on the surface. Accordingly, it is similarly possible to examine the exact chemical state of rubber on the surface of a rubber material both before and after deterioration; moreover, a comparison of the peak intensities or areas before and after deterioration also enables to examine deterioration (deterioration degree).

Since it is difficult for the NEXAFS method to perform an absolute measurement, the measurement results cannot be simply compared between samples. Then, for example, the X-ray absorption spectra of a rubber material can be measured and analyzed using the electron yield method in the following manner to accurately analyze the deterioration degree (%), the contribution rates (%) of oxygen deterioration and ozone deterioration, and the amount of oxygen and ozone bonded (deterioration indicator).

Specifically, a method may be performed which includes: calculating normalization constants $\alpha$ and $\beta$ using the following formula 2-1 on the basis of X-ray absorption spectra obtained by scanning over a required range of high intensity X-ray energies at the carbon K-shell absorption edge within the range of 260 eV to 400 eV; performing waveform separation of the X-ray absorption spectra at the carbon K-shell absorption edge corrected with the normalization constants $\alpha$ and $\beta$ to obtain peak areas derived from $\pi^*$ transition at around 285 eV; and determining the deterioration degree using the following formula 2-2 with the obtained peak areas:

[total area of X-ray absorption spectrum over measurement range of sample before deterioration]$\times\alpha=1$,and

[total area of X-ray absorption spectrum over measurement range of sample after deterioration]$\times\beta=1$;and (formula 2-1)

$[1-[(\text{peak area of }\pi^*\text{ after deterioration})\times\beta]/[(\text{peak area of }\pi^*\text{ before deterioration})\times\alpha]]\times100$=deterioration degree (%). (formula 2-2)

The measurement of a sample from which blooms are removed makes it possible to examine the exact chemical state on the surface of a rubber material both before and after deterioration. Moreover, a comparison between the individual spectra enables to calculate the deterioration degree (%) of the deteriorated rubber material; therefore, an accurate analysis of the deterioration rate can be made. More specifically, the analysis can be performed according to the method described in JP2012-141278A (which is incorporated by reference in its entirety).

Another method may be performed which includes: performing waveform separation of an X-ray absorption spectrum at the oxygen K-shell absorption edge obtained by scanning over a range of high intensity X-ray energies of 500 to 600 eV; and calculating contribution rates of oxygen deterioration and ozone deterioration using the following formula 2-3, wherein the oxygen deterioration corresponds to a peak on the low energy side with a peak top energy in the range of 532 to 532.7 eV, and the ozone deterioration corresponds to a peak on the high energy side with a peak top energy in the range of 532.7 to 534 eV:

[peak area of oxygen deterioration]/[(peak area of ozone deterioration)+(peak area of oxygen deterioration)]$\times100$=contribution rate (%) of oxygen deterioration,and

[peak area of ozone deterioration]/[(peak area of ozone deterioration)+(peak area of oxygen deterioration)]$\times100$=contribution rate (%) of ozone deterioration. (formula 2-3)

The measurement of a deteriorated sample from which blooms are removed makes it possible to examine the exact chemical state on the surface of a rubber material. Therefore, the contribution rates (%) of oxygen deterioration and ozone deterioration in the deteriorated rubber material can be calculated to make an accurate analysis of the contribution rate of each deterioration factor. More specifically, the analysis can be performed according to the method described in JP2012-141278A (which is incorporated by reference in its entirety).

Still another method may be performed which includes: determining a normalization constant $\gamma$ using the following formula 2-4 on the basis of an X-ray absorption spectrum at the carbon K-shell absorption edge after deterioration; and correcting a total peak area of the oxygen K-shell absorption edge with the normalization constant $\gamma$ based on the following formula 2-5 to determine the amount of oxygen and ozone bonded to the rubber material:

[total area of X-ray absorption spectrum at carbon K-shell absorption edge]$\times\gamma=1$;and (formula 2-4)

[peak area of oxygen K-shell absorption edge]$\times\gamma$=amount (index) of oxygen and ozone bonded. (formula 2-5)

The measurement of a deteriorated sample from which blooms are removed makes it possible to examine the exact chemical state on the surface of a rubber material. Therefore, the amount of oxygen and ozone bonded to the rubber material due to deterioration can be accurately measured and used as a deterioration indicator. More specifically, the analysis can be performed according to the method described in JP2012-141278A (which is incorporated by reference in its entirety).

EXAMPLES

Hereinafter, the present invention is more specifically described referring to Examples, but the present invention is not limited only to these Examples.

[Production of Test Tire]

(Step 1)

According to each formulation shown in Tables 1-1 and 1-2, the materials other than the sulfur and vulcanization accelerator were charged in a 1.7-L Banbury mixer manufactured by Kobe Steel, Ltd. so as to give a charging rate of 58%, and were then kneaded at 80 rpm until the temperature of the mixture reached 140° C.

(Step 2)

To the kneaded mixture obtained in Step 1, the sulfur and vulcanization accelerator were added, and the resulting mixture was kneaded for 3 minutes at 80° C. using an open roll mill. In this way, unvulcanized rubber compositions for a sidewall or tread (sidewalls 1 and 2, and treads 1 and 2) were obtained.

(Step 3)

The unvulcanized rubber composition for sidewall 1 and the unvulcanized rubber composition for tread 1 obtained in Step 2 were formed into a sidewall shape and a tread shape, respectively, and they were assembled with other tire components to form a tire, which was then vulcanized at 160° C. for 20 minutes to produce a test tire 1. Also, a test tire 2 was produced in the same manner as for the test tire 1, except that sidewall 2 was used in place of the sidewall 1 and tread 2 was used in place of the tread 1.

The materials used for the sidewalls 1 and 2 and treads 1 and 2 are as follows.

(Materials)

Natural rubber (NR): TSR20

Butadiene rubber (BR): BR150B manufactured by Ube Industries, Ltd.

Styrene-butadiene rubber (SBR): Nipol 1502 manufactured by Zeon Corp.

Carbon black N351: ShoBlack N351 ($N_2SA$: 71 $m^2/g$) manufactured by Cabot Japan K.K.

Silica: Ultrasil VN3 manufactured by Degussa

Silane coupling agent: Si69 (bis(3-triethoxysilylpropyl) tetrasulfide) manufactured by Degussa Oil: Process X-140 manufactured by Japan Energy Corp.

Phenylenediamine antioxidant: Nocrac 6C (N-1,3-dimethylbutyl-N'-phenyl-p-phenylenediamine) manufactured by Ouchi Shinko Chemical Industrial Co., Ltd.

Wax: Ozoace 0355 manufactured by Nippon Seiro Co., Ltd.

Zinc oxide: Ginrei R manufactured by Toho Zinc Co. Ltd.

Stearic acid: Tsubaki manufactured by NOF Corp.

Sulfur powder (containing 5% oil): 5% Oil treated sulfur powder (soluble sulfur containing 5% by mass of oil) manufactured by Tsurumi Chemical Industry Co., Ltd.

Vulcanization accelerator: Nocceler CZ (N-cyclohexyl-2-benzotiazylsulphenamide) manufactured by Ouchi Shinko Chemical Industrial Co., Ltd.

TABLE 1-1

| Sidewall formulation | | |
|---|---|---|
| | Sidewall 1 | Sidewall 2 |
| NR | 50 | 50 |
| BR | 50 | 50 |
| Carbon black N351 | 60 | 5 |
| Oil | 5 | 5 |
| Phenylenediamine antioxidant | 2 | 1 |
| Wax | 2.5 | 1 |
| Zinc oxide | 3 | 3 |
| Stearic acid | 2 | 2 |
| Sulfur powder | 1.2 | 1.2 |
| Vulcanization accelerator | 1 | 1 |

Unit: part(s) by mass

TABLE 1-1

| Tread formulation | | |
|---|---|---|
| | Tread 1 | Tread 2 |
| NR | 30 | 30 |
| SBR | 70 | 70 |
| Carbon black N351 | 30 | 10 |
| Silica | 60 | 80 |
| Silalne coupling agent | 3 | 3 |
| Oil | 10 | 10 |
| Phenylenediamine antioxidant | 4 | 3 |
| Wax | 2.5 | 1.5 |
| Zinc oxide | 3 | 3 |
| Stearic acid | 2 | 2 |
| Sulfur powder | 1.2 | 1.2 |
| Vulcanization accelerator | 1 | 1 |

Unit: part(s) by mass

Examples and Comparative Examples

A sample measuring about 2 mm×1 mm×0.5 mm was taken from each of the sidewall 1 and tread 1 of the test tire 1 deteriorated by urban area driving and the sidewall 2 and tread 2 of the test tire 2 deteriorated by urban area driving. Then, according to Table 1-3 or 1-4, a vapor deposited Au film was formed on the surface of each sample by a resistance heating vacuum vapor deposition method to prepare test samples. After the sample preparation, the samples were stored in a vacuum desiccator so as to prevent the effect of oxygen other than that due to deterioration from occurring.

(Apparatus Used)

NEXAFS: NEXAFS measurement apparatus provided with the beamline BL12 at Kyushu Synchrotron Light Research Center (SAGA-LS)

XPS: AXIS Ultra manufactured by Kratos Analytical

The deterioration degree (%) of each of the samples was measured by performing the following deterioration rate analysis using NEXAFS. Also, the contribution rates (%) of oxygen and ozone deterioration were measured by performing the following deterioration contribution rate analysis. Further, the deterioration indicator (index) was measured by performing the following deterioration indicator measurement. The NEXAFS measurement conditions were as follows.

Brilliance: $5\times10^{12}$ photons/s/mrad$^2$/mm$^2$/0.1% bw

Number of photons: $2\times10^9$ photons/s (Deterioration Rate Analysis)

Scanning was performed over a range of high intensity X-ray energies of 260 to 400 eV to obtain X-ray absorption spectra at the carbon K-shell absorption edge. Normalization constants $\alpha$ and $\beta$ were calculated using formula 1-1 based on the spectra over the required range of 260 to 350 eV, and then the spectra were normalized (corrected) with the obtained constants. The normalized spectra were subjected to waveform separation, and then the deterioration degree (%) was determined using formula 1-2 based on the resulting peak areas derived from $\pi^*$ transition at around 285 eV.

(Deterioration Contribution rate Analysis)

Scanning was performed over a range of high intensity

X-ray energies of 500 to 600 eV to obtain an X-ray absorption spectrum at the oxygen K-shell absorption edge. The spectrum was subjected to waveform separation, and then the contribution rates of oxygen deterioration and ozone deterioration were calculated using formula 1-3, wherein the oxygen deterioration corresponds to a peak on the low energy side with a peak top at 532 to 532.7 eV, and the ozone deterioration corresponds to a peak on the high energy side with a peak top at 532.7 to 534 eV.

(Deterioration Indicator Measurement)

The normalization constant $\gamma$ was determined using formula 1-4 based on the X-ray absorption spectrum at the carbon K-shell absorption edge after deterioration obtained in the deterioration rate analysis. The total peak area of the oxygen K-shell absorption edge was corrected (normalized) with the constant, whereby the amount of oxygen and ozone bonded to the polymer material (deterioration indicator) was determined based on formula 1-5.

The results obtained from the foregoing analyses are shown in Tables 1-3 and 1-4.

TABLE 1-3

| Sidewall | | |
|---|---|---|
| | Comparative Example 1-1 | Example 1-1 |
| Material | Sidewall 2 of test tire 2 | Sidewall 2 of test tire 2 |
| Thickness (Å) of vapor deposited metal (Au) film | 0 | 8 |
| Contribution rate (%) of ozone deterioration | Not measurable | 10 |
| Contribution rate (%) of oxygen deterioration | Not measurable | 90 |
| Deterioration degree (%) | Not measurable | 25 |
| Deterioration indicator | Not measurable | 0.21 |

TABLE 1-4

| Tread | | | | |
|---|---|---|---|---|
| | Comparative Example 1-2 | Example 1-2 | Comparative Example 1-3 | Example 1-3 |
| Material | Tread 1 of test tire 1 | Tread 1 of test tire 1 | Tread 1 of test tire 1 | Tread 2 of test tire 2 |
| Thickness (Å) of vapor deposited metal (Au) film | 0 | 8 | 500 | 8 |
| Contribution rate (%) of ozone deterioration | Not measurable | 32 | Not measurable | 21 |
| Contribution rate (%) of oxygen deterioration | Not measurable | 68 | Not measurable | 79 |
| Deterioration degree (%) | Not measurable | 34 | Not measurable | 29 |
| Deterioration indicator | Not measurable | 0.47 | Not measurable | 0.3 |

For each of the samples with no vapor deposited Au film formed thereon and the sample with a 500 Å-thick vapor deposited Au film formed thereon, none of the contribution rates of ozone and oxygen deterioration, the deterioration degree and the deterioration indicator (index) of the deteriorated samples was able to be analyzed. In contrast, in the Examples using a sample with a 8 Å-thick vapor deposited Au film formed thereon, these items were all able to be analyzed using NEXAFS. Consequently, the evaluation method according to the present invention was demonstrated to be effective.

Examples and Comparative Examples (Rubber Sample)

According to the following formulation, the materials other than the sulfur and vulcanization accelerator were charged in a 1.7-L Banbury mixer manufactured by Kobe Steel, Ltd. so as to give a charging rate of 58%, and were then kneaded at 80 rpm until the temperature of the mixture reached 140° C. (Step 1). To the kneaded mixture obtained in Step 1, the sulfur and vulcanization accelerator were added according to the following formulation, and the resulting mixture was vulcanized at 160° C. for 20 minutes to prepare a rubber sample (Step 2).

(Formulation)

Natural rubber: 50 parts by mass, butadiene rubber: 50 parts by mass, carbon black: 60 parts by mass, oil: 5 parts by mass, antioxidant: 2 parts by mass, wax: 2.5 parts by mass, zinc oxide: 3 parts by mass, stearic acid: 2 parts by mass, sulfur powder: 1.2 parts by mass, vulcanization accelerator: 1 part by mass (In Comparative Example 2-3, no wax and no antioxidant were added).

The materials used are as follows. The deteriorated rubber samples were prepared by deterioration under the following conditions.

Natural rubber: TSR20

Butadiene rubber: BR150B manufactured by Ube Industries, Ltd.

Carbon black: ShoBlack N351 manufactured by Cabot Japan K.K.

Oil: Process X-140 manufactured by Japan Energy Corp.

Antioxidant: Nocrac 6C (N-1,3-dimethylbutyl-N'-phenyl-p-phenylenediamine) manufactured by Ouchi Shinko Chemical Industrial Co., Ltd.

Wax: Ozoace 0355 manufactured by Nippon Seiro Co., Ltd.

Zinc oxide: Ginrei R manufactured by Toho Zinc Co. Ltd.

Stearic acid: Tsubaki manufactured by NOF Corp.

Sulfur powder (containing 5% oil): 5% Oil treated sulfur powder (soluble sulfur containing 5% by mass of oil) manufactured by Tsurumi Chemical Industry Co., Ltd.

Vulcanization accelerator: Nocceler CZ (N-cyclohexyl-2-benzotiazylsulphenamide) manufactured by Ouchi Shinko Chemical Industrial Co., Ltd.

(Deterioration Conditions)

Ozone deterioration: 40° C., 50 pphm (24 hours)

Oxygen deterioration: 80° C., oxygen:nitrogen=4:1 (168 hours)

The prepared rubber samples were each subjected to a pretreatment described in Table 2-1, and then subjected to NEXAFS measurement near the carbon K-shell absorption edge to obtain X-ray absorption spectra (NEXAFS spectra). In Example 2-4 and Comparative Example 2-6, XPS measurement was performed to obtain XPS spectra. FIG. 2-2 shows the NEXAFS spectra obtained in Example 2-1 and Comparative Examples 2-1 to 2-3.

(Apparatus Used)

NEXAFS: NEXAFS measurement apparatus provided with the beamline BL12 at Kyushu Synchrotron Light Research Center (SAGA-LS)

XPS: AXIS Ultra manufactured by Kratos Analytical

NEXAFS Measurement

The following deterioration rate analysis, deterioration contribution rate analysis and deterioration indicator measurement of each of the samples were performed using NEXAFS to measure the deterioration degree (%), the contribution rates (%) of oxygen and ozone deterioration and the deterioration indicator (index). The following evaluation of the information about rubber was performed to assess whether or not the obtained spectra were affected by blooms. The results thus obtained are shown in Table 2-1. The NEXAFS measurement conditions were as follows. In the measurement, the rubber samples were each processed with a microtome so as to have a thickness of 100 μm or less, and then stored in a vacuum desiccator.

(NEXAFS Measurement Conditions)

Brilliance: $5\times10^{12}$ photons/s/mrad$^2$/mm$^2$/0.1% bw

Number of photons: $2\times10^9$ photons/s (Deterioration Rate Analysis)

Scanning was performed over a range of high intensity X-ray energies of 260 to 400 eV to obtain X-ray absorption spectra at the carbon K-shell absorption edge. Normalization constants α and β were calculated using formula 2-1 based on the spectra over the required range of 260 to 350 eV, and then the spectra were normalized (corrected) with the obtained constants. The normalized spectra were subjected to waveform separation, and then the deterioration degree (%) was determined using formula 2-2 based on the resulting peak areas derived from π* transition at around 285 eV.

(Deterioration Contribution rate Analysis)

Scanning was performed over a range of high intensity X-ray energies of 500 to 600 eV to obtain an X-ray absorption spectrum at the oxygen K-shell absorption edge. The spectrum was subjected to waveform separation, and then the contribution rates of oxygen deterioration and ozone deterioration were calculated using formula 2-3, wherein the oxygen deterioration corresponds to a peak on the low energy side with a peak top at 532 to 532.7 eV, and the ozone deterioration corresponds to a peak on the high energy side with a peak top at 532.7 to 534 eV.

(Deterioration Indicator Measurement)

The normalization constant γ was determined using formula 2-4 based on the X-ray absorption spectrum at the carbon K-shell absorption edge after deterioration obtained in the deterioration rate analysis. The total peak area of the oxygen K-shell absorption edge was corrected (normalized) with the constant, whereby the amount of oxygen and ozone bonded to the rubber material (deterioration indicator) was determined based on formula 2-5.

(Information about Rubber)

The obtained NEXAFS spectra and XPS spectra were evaluated based on the following criteria as to whether or not the information about rubber was obtained without being affected by contamination by other carbon components such as wax.

o: Accurate information about the surface of a rubber material was obtained.

x: No accurate information about the surface of a rubber material was obtained.

TABLE 2-1

| | Comparative Example 2-1 | Comparative Example 2-2 | Comparative Example 2-3 | Comparative Example 2-4 | Comparative Example 2-5 | Comparative Example 2-6 |
|---|---|---|---|---|---|---|
| Rubber material sample | With wax & antioxidant | With wax & antioxidant | Without wax & antioxidant | With wax & antioxidant | With wax & antioxidant | With wax & antioxidant |
| Pretreatment | No pretreatment | Wiping the sample surface with waste | No pretreatment | No pretreatment | No pretreatment | No pretreatment |
| Solvent used in pretreatment | — | Acetone | — | — | — | — |
| Measurement method | NEXAFS | NEXAFS | NEXAFS | NEXAFS | NEXAFS | XPS |
| Whether or not rubber information was obtained without affected by contamination by other carbon components | X | X | ○ | X | X | Not assessable |
| Deterioration time (h)/ozone | 0 | 0 | 0 | 24 | 0 | 0 |
| Deterioration time (h)/oxygen under heat | 0 | 0 | 0 | 0 | 168 | 0 |
| Deterioration degree (%) | Not calculable | Not calculable | 0 | Not calculable | Not calculable | Not calculable |
| Contribution rate (%) of ozone deterioration | Not calculable | Not calculable | 0 | Not calculable | Not calculable | Not calculable |
| Contribution rate (%) of oxygen deterioration under heat | Not calculable | Not calculable | 0 | Not calculable | Not calculable | Not calculable |
| Deterioration indicator | Not calculable | Not calculable | 0 | Not calculable | Not calculable | Not calculable |

| | Example 2-1 | Example 2-2 | Example 2-3 | Example 2-4 |
|---|---|---|---|---|
| Rubber material sample | With wax & antioxidant | With wax & antioxidant | With wax & antioxidant | With wax & antioxidant |
| Pretreatment | Soxhlet extraction for 24 hours | Soxhlet extraction for 24 hours | Soxhlet extraction for 24 hours | Soxhlet extraction for 24 hours |
| Solvent used in pretreatment | Acetone | Acetone | Acetone | Acetone |
| Measurement method | NEXAFS | NEXAFS | NEXAFS | XPS |
| Whether or not rubber information was obtained without affected by contamination by other carbon components | ○ | ○ | ○ | ○ |
| Deterioration time (h)/ozone | 0 | 24 | 0 | 24 |
| Deterioration time (h)/oxygen under heat | 0 | 0 | 168 | 0 |
| Deterioration degree (%) | 0 | 69 | 32 | — |
| Contribution rate (%) of ozone deterioration | 0 | 100 | 0 | — |
| Contribution rate (%) of oxygen deterioration under | 0 | 0 | 100 | — |
| Deterioration indicator | 0 | 0.51 | 0.21 | — |

In the spectrum of Comparative Example 2-3 shown in FIG. 2-2, in which the sample to be measured was formulated so as not to allow blooming of carbon contaminants on the sample surface, the C═C bond in rubber was detected. On the other hand, in Comparative Example 2-1 in which no pretreatment was performed, no C═C bond was detected, but instead the intensity of C—H bond was increased, which demonstrated that the C—H bond in the wax covering the surface was detected, but no C═C bond in rubber was detected. In Comparative Example 2-2 in which the surface of the sample was wiped with waste, the intensity of C═C bond was somewhat increased and the intensity of C—H bond was somewhat decreased; however, the amount of C═C bond detected was smaller as compared with Comparative Example 2-3, which means that the wax blooming on the surface was not able to be removed and thus accurate measurement was not able to be performed.

In contrast, in Example 2-1, the C═C bond and the C—H bond were detected in amounts comparable to those in Comparative Example 2-3. This demonstrated that the wax blooming on the surface was able to be sufficiently removed and thus the chemical state on the rubber surface was able to be accurately measured. Also in the XPS measurement in Example 2-4, accurate measurement was able to be performed. Furthermore, the deterioration degree and others were not able to be calculated for the deteriorated rubber samples of Comparative Examples 2-4 and 2-5 to which no pretreatment was applied, whereas the deterioration degree and others were able to be calculated for the deteriorated rubber samples of Examples 2-2 and 2-3 in which blooms were removed by the pretreatment.

The invention claimed is:

1. A deterioration analysis method, comprising irradiating a tire rubber composition with a metal coating having a thickness of 100 Å or less formed thereon, with high intensity X-rays, and measuring X-ray absorption while varying the energy of the X-rays, to analyze deterioration of the tire rubber composition.

2. The deterioration analysis method according to claim 1, wherein the metal coating is a vapor deposited metal film.

3. The deterioration analysis method according to claim 1, wherein the tire rubber composition has a carbon black content of 50 parts by mass or less per 100 parts by mass of a rubber component of the tire rubber composition.

4. A deterioration measurement method, comprising removing blooms on a surface of a tire rubber composition and then applying an X-ray-based surface analysis method to measure deterioration on the surface of the tire rubber composition.

5. The deterioration measurement method according to claim 4, examining a change in deterioration on the surface of the tire rubber composition.

6. The deterioration measurement method according to claim 4, wherein the blooms on the surface of the tire rubber composition are removed using a solvent.

7. The deterioration measurement method according to claim 6, wherein the solvent is an organic solvent.

8. The deterioration measurement method according to claim 4, wherein the blooms on the surface of the tire rubber composition are removed using a solvent extraction method.

* * * * *